US008032223B2

(12) United States Patent
Imran

(10) Patent No.: US 8,032,223 B2
(45) Date of Patent: Oct. 4, 2011

(54) RANDOMIZED STIMULATION OF A GASTROINTESTINAL ORGAN

(75) Inventor: Mir A. Imran, Los Altos Hills, CA (US)

(73) Assignee: IntraPace, Inc., Mountain View, CA (US)

( * ) Notice: Subject to any disclaimer, the term of this patent is extended or adjusted under 35 U.S.C. 154(b) by 0 days.

(21) Appl. No.: 12/572,067

(22) Filed: Oct. 1, 2009

(65) Prior Publication Data

US 2010/0023087 A1 Jan. 28, 2010

Related U.S. Application Data

(62) Division of application No. 11/219,004, filed on Sep. 1, 2005, now Pat. No. 7,616,996.

(51) Int. Cl.
*A61N 1/00* (2006.01)

(52) U.S. Cl. ........................................................ 607/40

(58) Field of Classification Search ............. 607/40–41, 607/72–73, 133, 138, 116; 600/29–30
See application file for complete search history.

(56) References Cited

U.S. PATENT DOCUMENTS

| | | | |
|---|---|---|---|
| 3,411,507 A | 11/1968 | Wingrove | |
| 3,646,940 A | 3/1972 | Timm et al. | |
| 3,662,758 A | 5/1972 | Glover | |
| 3,677,251 A | 7/1972 | Bowers | |
| 3,735,766 A | 5/1973 | Bowers et al. | |
| 3,796,221 A | 3/1974 | Hagfors | |
| 3,815,611 A | 6/1974 | Denniston, III | |
| 3,835,865 A | 9/1974 | Bowers | |
| 4,102,344 A | 7/1978 | Conway et al. | |
| 4,135,518 A | 1/1979 | Dutcher | |
| 4,153,059 A * | 5/1979 | Fravel et al. | 607/41 |
| RE30,366 E | 8/1980 | Rasor et al. | |
| 4,338,945 A * | 7/1982 | Kosugi et al. | 607/46 |
| 4,431,000 A * | 2/1984 | Butler et al. | 607/73 |
| 4,571,556 A * | 2/1986 | Gnerlich et al. | 331/78 |
| 4,628,928 A | 12/1986 | Lowell | |
| 4,688,574 A * | 8/1987 | Dufresne et al. | 607/59 |
| 4,690,145 A * | 9/1987 | King-Smith et al. | 607/63 |
| 4,699,143 A * | 10/1987 | Dufresne et al. | 607/46 |
| 4,823,808 A | 4/1989 | Clegg et al. | |
| 4,921,481 A | 5/1990 | Danis et al. | |
| 4,925,446 A | 5/1990 | Garay et al. | |
| 5,111,816 A | 5/1992 | Pless et al. | |
| 5,112,310 A | 5/1992 | Grobe | |
| 5,188,104 A | 2/1993 | Wernicke et al. | |

(Continued)

FOREIGN PATENT DOCUMENTS

EP 0 129 483 2/1984

(Continued)

OTHER PUBLICATIONS

Bellahsene, et al., "Evaluation of a Portable Gastric Stimulator," Ninth Annual Conference of the Engineering in Medicine and Biology Society, 2 pages total. (1987).

(Continued)

*Primary Examiner* — Mark W Bockelman
*Assistant Examiner* — Roland Dinga
(74) *Attorney, Agent, or Firm* — Kilpatrick Townsend & Stockton LLP

(57) ABSTRACT

A device, system and method for stimulating a digestive organ is provided where the stimulation is randomized.

10 Claims, 6 Drawing Sheets

U.S. PATENT DOCUMENTS

| | | | |
|---|---|---|---|
| 5,197,491 A | 3/1993 | Anderson et al. | |
| 5,217,449 A | 6/1993 | Yuda et al. | |
| 5,248,302 A | 9/1993 | Patrick et al. | |
| 5,259,399 A | 11/1993 | Brown | |
| 5,285,781 A | 2/1994 | Brodard | |
| 5,292,344 A | 3/1994 | Douglas | |
| 5,411,527 A | 5/1995 | Alt | |
| 5,415,181 A | 5/1995 | Hogrefe et al. | |
| 5,423,872 A | 6/1995 | Cigaina | |
| 5,540,730 A | 7/1996 | Terry, Jr. et al. | |
| 5,558,640 A | 9/1996 | Pfeiler et al. | |
| 5,681,260 A | 10/1997 | Ueda et al. | |
| 5,690,691 A * | 11/1997 | Chen et al. | 607/40 |
| 5,716,392 A | 2/1998 | Bourgeois et al. | |
| 5,792,048 A | 8/1998 | Schaefer | |
| 5,800,445 A | 9/1998 | Ratcliff et al. | |
| 5,836,994 A | 11/1998 | Bourgeois | |
| 5,861,014 A | 1/1999 | Familoni | |
| 5,902,331 A | 5/1999 | Bonner et al. | |
| 5,928,195 A | 7/1999 | Malamud et al. | |
| 5,935,107 A | 8/1999 | Taylor et al. | |
| 5,993,473 A | 11/1999 | Chan et al. | |
| 5,995,872 A | 11/1999 | Bourgeois | |
| 6,004,319 A | 12/1999 | Goble et al. | |
| 6,026,326 A | 2/2000 | Bardy | |
| 6,030,364 A | 2/2000 | Durgin et al. | |
| 6,041,258 A | 3/2000 | Cigaina et al. | |
| 6,083,249 A | 7/2000 | Familoni | |
| 6,091,992 A | 7/2000 | Bourgeois et al. | |
| 6,097,984 A | 8/2000 | Douglas | |
| 6,098,629 A | 8/2000 | Johnson et al. | |
| 6,104,955 A | 8/2000 | Bourgeois | |
| 6,112,123 A | 8/2000 | Kelleher et al. | |
| 6,115,635 A | 9/2000 | Bourgeois | |
| 6,205,359 B1 | 3/2001 | Boveja | |
| 6,216,039 B1 | 4/2001 | Bourgeois | |
| 6,243,607 B1 | 6/2001 | Mintchev et al. | |
| 6,285,897 B1 | 9/2001 | Kilcoyne et al. | |
| 6,321,124 B1 | 11/2001 | Cigaina | |
| 6,327,503 B1 | 12/2001 | Familoni | |
| 6,366,814 B1 | 4/2002 | Boveja et al. | |
| 6,381,495 B1 | 4/2002 | Jenkins | |
| 6,427,089 B1 | 7/2002 | Knowlton | |
| 6,449,511 B1 | 9/2002 | Mintchev et al. | |
| 6,453,199 B1 | 9/2002 | Kobozev | |
| 6,454,785 B2 | 9/2002 | De Hoyos Garza | |
| 6,477,423 B1 | 11/2002 | Jenkins | |
| 6,510,332 B1 | 1/2003 | Greenstein | |
| 6,529,778 B2 | 3/2003 | Prutchi | |
| 6,535,764 B2 | 3/2003 | Imran et al. | |
| 6,540,789 B1 | 4/2003 | Silverman et al. | |
| 6,542,776 B1 | 4/2003 | Gordon et al. | |
| 6,564,101 B1 * | 5/2003 | Zikria | 607/40 |
| 6,571,127 B1 | 5/2003 | Ben-Haim et al. | |
| 6,591,137 B1 | 7/2003 | Fischeli et al. | |
| 6,600,953 B2 | 7/2003 | Flesler et al. | |
| 6,606,518 B1 | 8/2003 | Cigaina | |
| 6,606,523 B1 | 8/2003 | Jenkins | |
| 6,609,025 B2 | 8/2003 | Barrett et al. | |
| 6,611,715 B1 | 8/2003 | Boveja | |
| 6,615,084 B1 | 9/2003 | Cigaina | |
| 6,684,104 B2 | 1/2004 | Gordon et al. | |
| 6,826,428 B1 | 11/2004 | Chen et al. | |
| 6,879,859 B1 | 4/2005 | Boveja | |
| 6,895,278 B1 | 5/2005 | Gordon et al. | |
| 6,895,279 B2 | 5/2005 | Loeb et al. | |
| 6,999,819 B2 | 2/2006 | Swoyer et al. | |
| 7,020,526 B1 | 3/2006 | Zhao | |
| 7,054,692 B1 | 5/2006 | Whitehurst et al. | |
| 7,120,498 B2 | 10/2006 | Imran et al. | |
| 7,255,675 B2 | 8/2007 | Gertner et al. | |
| 7,509,175 B2 | 3/2009 | Sparks et al. | |
| 7,616,996 B2 | 11/2009 | Imran | |
| 7,687,501 B2 | 3/2010 | Bennett et al. | |
| 7,702,394 B2 | 4/2010 | Imran | |
| 2002/0055757 A1 | 5/2002 | de la Torre et al. | |
| 2002/0072780 A1 | 6/2002 | Foley | |
| 2002/0103424 A1 | 8/2002 | Swoyer et al. | |
| 2002/0103521 A1 | 8/2002 | Swoyer et al. | |
| 2002/0103522 A1 | 8/2002 | Swoyer et al. | |
| 2002/0161414 A1 | 10/2002 | Flesler et al. | |
| 2002/0198570 A1 | 12/2002 | Puskas | |
| 2002/0198571 A1 | 12/2002 | Puskas | |
| 2003/0055463 A1 | 3/2003 | Gordon et al. | |
| 2003/0120328 A1 | 6/2003 | Jenkins et al. | |
| 2003/0144708 A1 | 7/2003 | Starkebaum | |
| 2003/0195600 A1 | 10/2003 | Tronnes | |
| 2003/0212439 A1 | 11/2003 | Schuler et al. | |
| 2004/0015201 A1 | 1/2004 | Greenstein | |
| 2004/0059393 A1 | 3/2004 | Policker et al. | |
| 2004/0088022 A1 | 5/2004 | Chen | |
| 2004/0093039 A1 | 5/2004 | Schumert | |
| 2004/0133089 A1 | 7/2004 | Kilcoyne et al. | |
| 2004/0147816 A1 | 7/2004 | Policker et al. | |
| 2004/0162595 A1 | 8/2004 | Foley | |
| 2004/0167583 A1 | 8/2004 | Knudson et al. | |
| 2004/0172084 A1 | 9/2004 | Knudson et al. | |
| 2004/0172085 A1 | 9/2004 | Knudson et al. | |
| 2004/0172086 A1 | 9/2004 | Knudson et al. | |
| 2004/0172088 A1 | 9/2004 | Knudson et al. | |
| 2004/0172095 A1 | 9/2004 | Jenkins et al. | |
| 2004/0176812 A1 | 9/2004 | Knudson et al. | |
| 2004/0236381 A1 | 11/2004 | Dinsmoor et al. | |
| 2004/0236382 A1 | 11/2004 | Dinsmoor et al. | |
| 2005/0021101 A1 | 1/2005 | Chen et al. | |
| 2005/0038454 A1 | 2/2005 | Loshakove | |
| 2005/0049655 A1 | 3/2005 | Boveja et al. | |
| 2005/0055039 A1 | 3/2005 | Burnett et al. | |
| 2005/0065575 A1 * | 3/2005 | Dobak | 607/45 |
| 2005/0089571 A1 | 4/2005 | Beckert et al. | |
| 2005/0090873 A1 | 4/2005 | Imran | |
| 2005/0096514 A1 | 5/2005 | Starkebaum | |
| 2005/0113880 A1 | 5/2005 | Gordon et al. | |
| 2005/0131485 A1 | 6/2005 | Knudson et al. | |
| 2005/0131486 A1 | 6/2005 | Boveja et al. | |
| 2005/0131487 A1 | 6/2005 | Boveja et al. | |
| 2005/0137643 A1 | 6/2005 | Mintchev | |
| 2005/0137644 A1 | 6/2005 | Boveja et al. | |
| 2005/0143784 A1 | 6/2005 | Imran | |
| 2005/0149141 A1 | 7/2005 | Starkebaum | |
| 2005/0149142 A1 | 7/2005 | Starkebaum | |
| 2005/0149146 A1 | 7/2005 | Boveja et al. | |
| 2005/0159800 A1 | 7/2005 | Marshall et al. | |
| 2005/0159801 A1 | 7/2005 | Marshall et al. | |
| 2005/0222637 A1 | 10/2005 | Chen | |
| 2005/0222638 A1 | 10/2005 | Foley | |
| 2005/0251219 A1 | 11/2005 | Evans | |
| 2006/0020298 A1 | 1/2006 | Camilleri et al. | |
| 2006/0025654 A1 | 2/2006 | Suzuki et al. | |
| 2006/0036293 A1 | 2/2006 | Whitehurst et al. | |
| 2006/0058851 A1 | 3/2006 | Cigaina | |
| 2006/0074335 A1 | 4/2006 | Ben-Oren et al. | |
| 2006/0074450 A1 | 4/2006 | Boveja et al. | |
| 2006/0074457 A1 | 4/2006 | Imran et al. | |
| 2006/0074458 A1 | 4/2006 | Imran | |
| 2006/0085054 A1 | 4/2006 | Zikorus et al. | |
| 2006/0089571 A1 | 4/2006 | Gertner | |
| 2006/0089690 A1 | 4/2006 | Gerber | |
| 2006/0089699 A1 | 4/2006 | Imran | |
| 2006/0095078 A1 | 5/2006 | Tronnes | |
| 2006/0116736 A1 | 6/2006 | DiLorenzo | |

FOREIGN PATENT DOCUMENTS

| | | |
|---|---|---|
| EP | 0 571 938 | 12/1993 |
| WO | WO 98/43700 | 10/1998 |
| WO | WO 98/53878 | 12/1998 |
| WO | WO 00/30534 | 6/2000 |
| WO | WO 01/58389 | 8/2001 |
| WO | WO 01/76690 | 10/2001 |
| WO | WO 02/26101 | 4/2002 |

OTHER PUBLICATIONS

Cigaina et al., "Gastric Myo-Electrical Pacing As Therapy For Morbid Obesity: Preliminary Results," Obes Surg;9:333-334, (1999).

Daniel et al., "Electrical Activity of the Gastrointestinal Tract as an Indication of Mechanical Activity," Am. J. of Digestive Diseases, 8(1):54-102, (1963).

Eagon et al., "Effects of Gastric Pacing on Canine Gastric Motility and Emptying," The American Physiological Society, 265(4):G767-G774, (Oct. 1993).

Eagon et al., "Gastrointestinal Pacing, Surgical Clinics of North America," 73(6): 1161-1172 (Dec. 1993).

Electric Stimulation of the Gastrointestinal Tract, GP, p. 151 (Apr. 1964).

Familoni, "Efficacy of Electrical Stimulation at Frequencies Higher Than Basal Rate in Canine Stomach," Digestive Diseases and Sciences, 42(5):892-897, (May 1997).

Familoni, et al., "Electrical Pacing of the Stomach in Dogs, Engineering in Medicine and Biology Society," IEEE Proceedings of the Annual International Conference, 6:2315-2316 (Oct. 29-Nov. 1, 1992).

Geldof et al., "Electrogastrographic Study of Gastric Myoelectrical Activity In Patients With Unexplained Nausea And Vomiting," Gut, 27:799808, (1986).

Hocking, "Postoperative Gastroparesis and TachygastriaResponse to Electric Stimulation and Erythromycin," Surgery, 114(3):538-542 (Sep. 1993).

Joshi et al., "Anesthesia for Laparoscopic Surgery," Canadian Journal of Anesthesia 49(6):R1-R5 (2002).

Kelly et al., "Role of the Gastric Pacesetter Potential Defined by Electrical Pacing," Canadian J. of Physiology and Pharmacology, 50:1017-1019, (1972).

Kelly, Differential Responses Of The Canine Gastric Corpus And Antrum To Electric Stimulation, Am. J. of Physiology. 226(1):230-234, (Jan. 1974).

Kelly, et al., "Pacing The Canine Stomach With Electric Stimulation," Am. J. of Physiology, 222(3):588-594 (Mar. 1972).

Kubota, et al., "Manometric Evaluation Of Children With Chronic Constipation Using a Suction-Stimulating Electrode," Eur. J. Pediari. Surg. 2:287-290, (1992).

Miedema et al., "Pacing The Human Stomach," Surgery, 143-150, (Feb. 1992).

Sarna et al., "Electrical Stimulation of Gastric Electrical Control Activity," Am. 1. of Physiology, 225(1):125-131, (Jul. 1973).

Sarna, et al., "Gastric Pacemakers," Gastroenterology. 70:226-231, (1976).

Swain, et al., "An Endoscopically Deliverable Tissue-Transfixing Device For Securing Biosensors In The Gastrointestinal Tract," Gastrointestinal Endoscopy, 40(6):730-734 (1994).

* cited by examiner

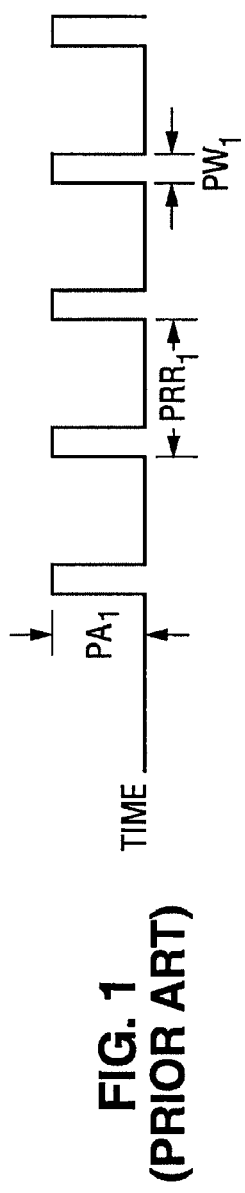
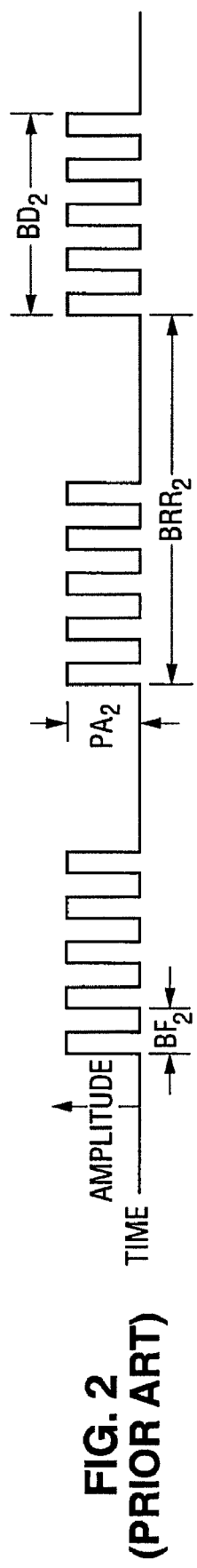
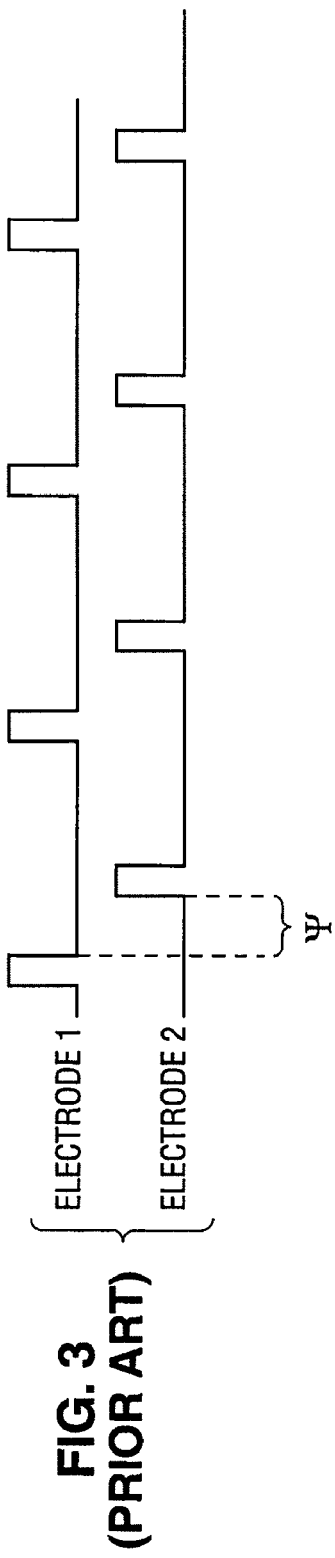
FIG. 1 (PRIOR ART)
FIG. 2 (PRIOR ART)
FIG. 3 (PRIOR ART)

RANDOMIZED STIMULATION OF A GASTROINTESTINAL ORGAN

CROSS-REFERENCES TO RELATED APPLICATIONS

The present application is a Divisional of U.S. Ser. No. 11/219,004 filed Sep. 1, 2005, which is incorporated herein by reference in their entirety.

BACKGROUND OF THE INVENTION

1. Field of the Invention

This invention relates to a device system and method for stimulating the stomach wall.

2. Background of the Invention

A number of devices have been proposed to stimulate the stomach wall of a stomach and other gastrointestinal organs. A variety of different stimulation parameters have been proposed.

However, there is belief that with existing proposed devices and stimulation parameters the stomach gastrointestinal or other digestive organs will adapt or become desensitized to stimulation, especially if such stimulation is delivered at non-physiologic rates for a relatively long time. Accordingly it would be desirable to provide a digestive organ stimulation device, system and/or method that may reduce adaptation or desensitization to stimulation.

Some devices have proposed using multiple electrodes in a phased relationship for stimulating digestive tract organs, in some cases, along a peristaltic flow path. However, there is also some belief that the stomach, gastrointestinal, or other digestive organs will adapt to such phased stimulation over time. Accordingly, it would be desirable to provide a digestive organ stimulation device, system and/or method that may reduce adaptation and/or desensitization to stimulation with multiple electrodes.

BRIEF SUMMARY OF THE INVENTION

The present invention provides a device, system and method for randomized stimulation of a digestive organ.

One aspect of the invention provides a device system and method directed to reducing adaptation or desensitization for a digestive organ to electrical stimulation. According to one aspect of the invention, a device is provided that is programmed to pseudorandomly select stimulation parameters and to deliver pseudorandom stimulation to a digestive organ. Pseudorandom as used herein is intended to include random selection within preset criteria or constraints. Such constraints or criteria may include, for example, stimulation within pre-selected or predetermined stimulation parameter windows.

The present invention includes those inventions as claimed in the claims set forth herein.

Various embodiments and various aspects of the invention are described in the following detailed description.

BRIEF DESCRIPTION OF THE DRAWINGS

FIG. 1 is a schematic illustration of an exemplary stimulation signal that has been applied to digestive organs.

FIG. 2 is a schematic illustration of an exemplary stimulation signal that has been applied to digestive organs.

FIG. 3 is a schematic illustration of exemplary phased stimulation using a plurality of electrodes.

DETAILED DESCRIPTION OF THE INVENTION

Figure 4:
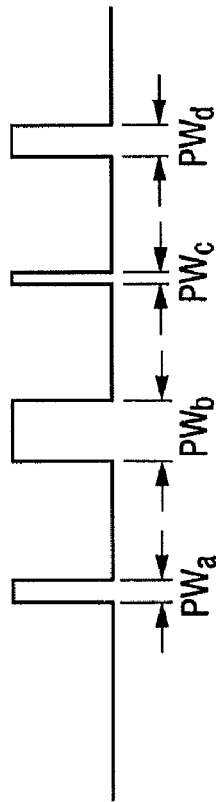
FIG. 4 is a schematic illustration of a stimulation signal in accordance with the invention.

According to one aspect of the invention a device for stimulating a digestive organ is provided. The device may stimulate any one or more digestive organs, including for example, portions of the gastrointestinal tract, or digestive organs that secrete digestive substances, digestive regulating hormones, or the like. According to one embodiment, a device for stimulating a stomach is provided.

Stimulation may be provided to elicit one or more desired effects or responses. Stimulation may be provided to control digestion, create sensation of satiety, to control movement of food within the gastrointestinal tract, to regulate digestive processes or to regulate hunger, among other things. One example of such a stimulating device is described in U.S. Pat. No. 6,535,764, incorporated herein by reference.

According to one aspect of the invention, a device is provided that is programmed to randomly (or pseudorandomly) select or vary one or more stimulation parameters, and to deliver the stimulation to a digestive organ according to the selected parameters. In accordance with one aspect, stimulation is randomly (or pseudorandomly) selected or varied to reduce adaptation or desensitization of a digestive organ to stimulation, and especially to stimulation at non-physiologic rates.

The programmed device may randomly (or pseudorandomly) select or generate parameters from within a window of acceptable parameters or a randomization window. Such parameters may include but are not limited to, e.g., pulse width, pulse repetition rate, burst frequency, burst repetition rate, pulses per burst. The programmed device may also randomly (or pseudorandomly) select or vary pulse amplitude, pulse shape and burst envelope within a window or according to selection criteria. The programmed device may randomly (or pseudorandomly) select or vary any one or more of these or other parameters prior to or during stimulation.

The programmed device may also randomly (or pseudorandomly) select or vary stimulation from pulse to pulse or burst to burst. The programmed device may operate to periodically change parameters or may do so in response to sensing or receiving feedback that adaptation or desensitization is occurring, or that the stimulation is otherwise losing its effectiveness. According to one aspect of the invention, for example, the device may monitor stimulation response over time using a contraction monitoring device such as a strain gauge or other contraction sensor. If the device detects a sub optimal stimulation response, the device may then randomly or pseudorandomly select the next parameter(s) or sets of parameters.

According to another aspect of the invention the programmed device may randomly (or pseudorandomly) select or vary stimulation at multiple stimulation sites. Each of such sites may have electrically separate stimulating electrodes where the stimulation parameter at each site is independent of the stimulation at the other sites. The stimulation sequence or timing of the sequence may also be randomly (or pseudorandomly) selected or varied. Thus, there is no specific phasing of stimulation at the various sites.

Referring to FIG. 1, an example of a typical stimulation signal that has been used to stimulate digestive organs is illustrated. The signal comprises a series of pulses. The pulses have a pulse amplitude of PA1, a pulse width of PW1 and repeat at a pulse repetition rate of PRR1. The pulse repetition rate is the time of initiation of a pulse to the time of initiation of the next pulse. The parameters are generally preset or otherwise selected or chosen for treatment.

Referring to FIG. 2, an example of a typical stimulation signal that has been used to stimulate digestive tract organs is illustrated. The signal comprises a pattern of repeating bursts of pulses that repeat at a burst repetition rate of BRR2. That is, the burst repetition rate is the time of the initiation of a burst to the initiation of a subsequent burst. The pulses within the burst have a pulse amplitude of PA and burst frequency of BF2. The bursts have a duration of BD2 and include a certain number of pulses per bursts PPB2. Theses parameters are generally preset or otherwise selected for treatment.

Referring to FIG. 3, an example of typical multi-electrode' stimulation is illustrated. A stimulation signal is delivered through Electrode 1. Stimulation at Electrode 2 is phased from the stimulation signal at Electrode 1 at phase angle, T, which represents a time between which the signal at Electrode 1 is initiated and the signal at Electrode 2 is initiated. The signal at Electrode 1 and Electrode 2 may also overlap.

FIG. 4 illustrates an example of a randomized stimulation signal that, in accordance with the invention, may be randomly (or pseudorandomly) selected by a programmed device and delivered to a digestive organ. The signal illustrated in FIG. 4 randomly varies in pulse width the first pulse width is PWa, the second is PWb, the third is PWc and the fourth is PWd. These pulse widths are selected and delivered. The pulse widths may be in a pre-selected range of pulse widths. For example in one variation they may vary from 1-20 pulses per minute.

Figure 5:
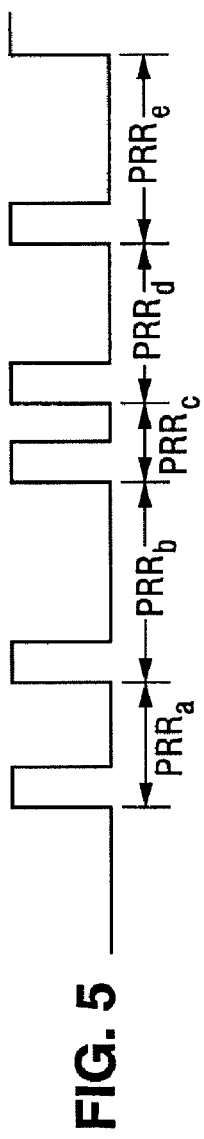
FIG. 5 is a schematic illustration of a stimulation signal in accordance with the invention.

FIG. 5 illustrates an example of a signal that may be randomly (or pseudorandomly) selected by a programmed device and delivered by a device or system in accordance with the invention. The pulses repeat at varying and random rates. The first pulse has a pulse repetition rate of PRRa after which the second pulse is initiated. The second pulse has a pulse repetition rate of PRRb after which the third pulse is initiated. The third pulse has a pulse repetition rate of PRRc after which the fourth pulse is initiated. The fourth pulse has a pulse repetition rate of PRRd after which the fifth pulse is initiated. The fifth pulse has a pulse repetition rate of PRRe after which the sixth pulse is initiated. The pulse widths or other parameters may or may not vary as well.

Figure 6:
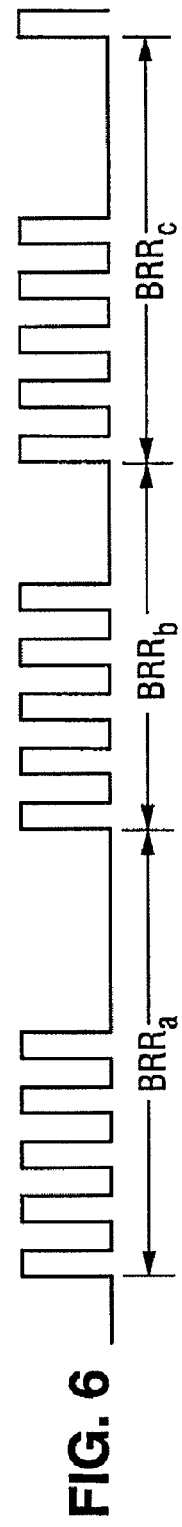
FIG. 6 is a schematic illustration of a stimulation signal in accordance with the invention.

FIG. 6 illustrates an example of a randomized signal that may be randomly (or pseudorandomly) selected and delivered by a programmed device or system or in accordance with a method of the invention. The stimulation signal comprises a series of bursts of pulses. The bursts of pulses repeat at varying randomized rates. The first burst has a burst repetition rate of BRRa, the second burst has a burst repetition rate of BRRb and the third burst has a burst repetition rate of BRRc. The burst frequency or other parameters may vary as well.

Figure 7:
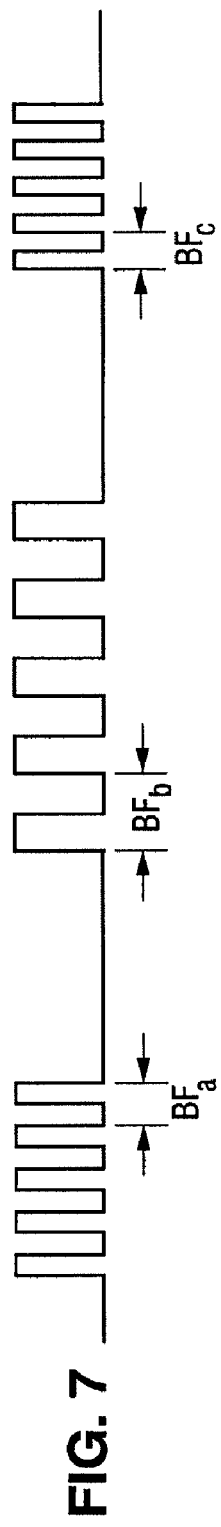
FIG. 7 is a schematic illustration of a stimulation signal in accordance with the invention.

FIG. 7 illustrates an example of a randomized signal that may be randomly (or pseudorandomly) selected and delivered by a programmed device or system in accordance with the invention. The stimulation signal comprises a series of bursts of pulses. The frequency of the bursts is randomly varied. The first burst of pulses has a frequency of BFa, the second burst of pulses has a frequency of BFb and the third burst of pulses has a frequency of BFc. Other parameters may vary as well.

Figure 8:
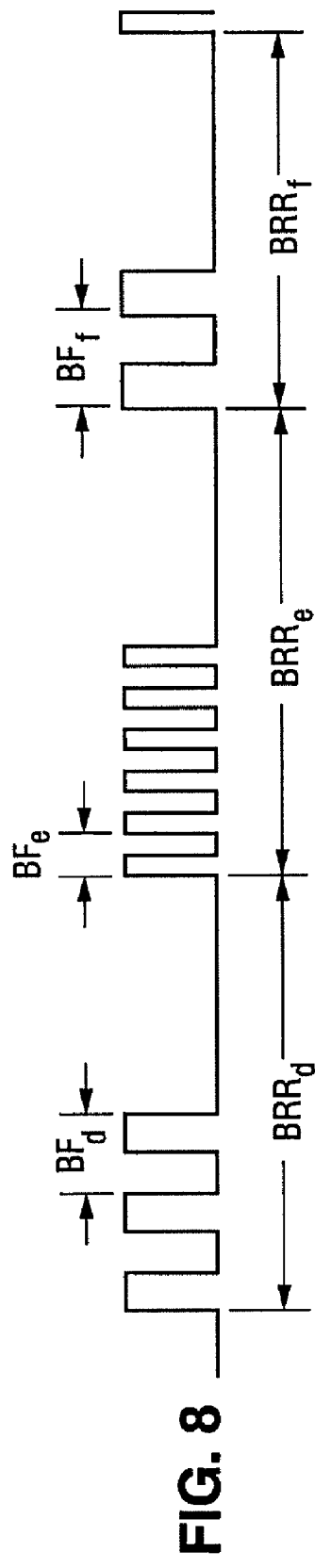
FIG. 8 is a schematic illustration of a stimulation signal in accordance with the invention.

FIG. 8 illustrates an example of a randomized signal that may be randomly (or pseudorandomly) selected and delivered by a device of system or in accordance with the invention. The stimulation signal comprises a series of bursts of pulses. Both the frequency of the pulses and the burst repetition rate randomly vary. The first burst has a frequency of BFd and a burst repetition rate of BRRd. The second burst has a frequency of BFe and a burst repetition rate of BRRe. The third burst has a frequency of BFf and a burst repetition rate of BRRf.

The randomized signals illustrated in FIG. 4-8 are examples of some parameters that may be randomized in a stimulation signal protocol. Any one or more of these parameters may be randomized in any one treatment protocol. The randomized parameters may include but are not limited to one or more of the following: pulse width, pulse amplitude, pulse repetition rate, burst frequency, burst repetition rate. Also, the shape of each pulse including pulses within a burst may vary. The shape of the envelope of pulses of a burst may vary. The frequency, pulse widths and amplitudes within a burst of pulses may also vary. Also, some parameters may vary while others are held constant.

The various randomized parameters may be randomly (or pseudorandomly) selected from within a window or group of parameters by a random number generator or controller. The window or group of parameters may be preprogrammed into the stimulation device and randomly selected during treatment.

Figure 9:
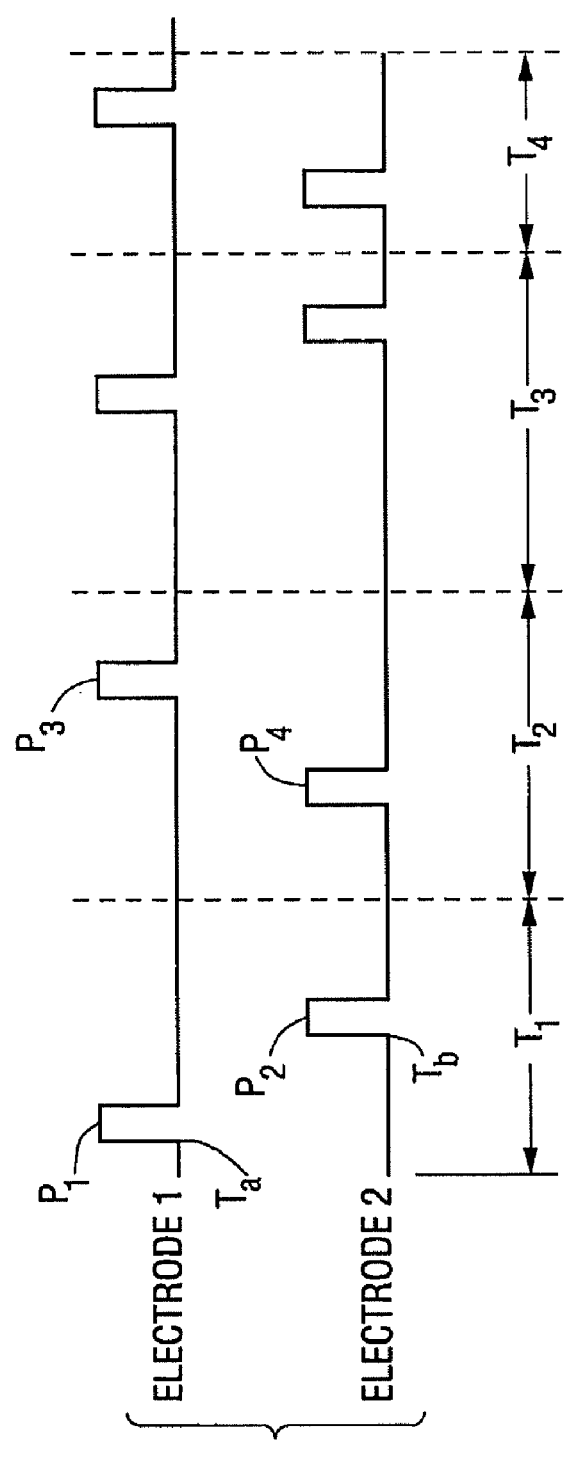
FIG. 9 is a schematic illustration of a stimulation signal in accordance with the invention.

FIG. 9 illustrates randomization of signals such as those described with respect to FIGS. 4-8, applied randomly at a plurality of electrode sites. As shown in FIG. 9 a first pulse p1 is applied at electrode 1 at time to and a second pulse is applied at electrode 2 p2 at time tb within the first time period t1. Within time period t2, a pulse p3 is applied at electrode 1 and a pulse p4 is applied electrode 2 at randomly different times. Similarly pulses at electrodes 1 and 2 are applied at different times during time periods t3 and t4.

Figure 12:
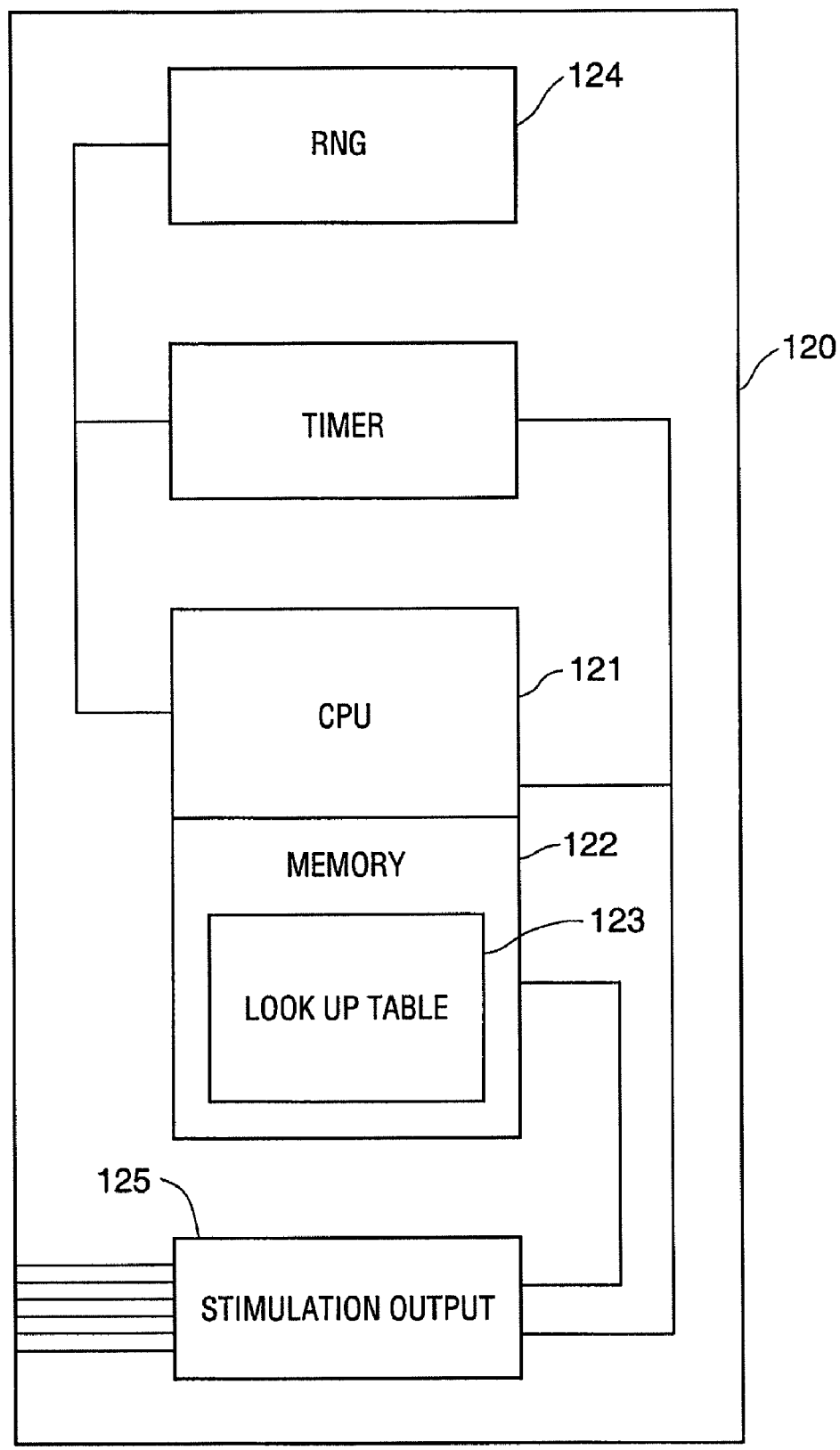
FIG. 12 is a stimulation device in accordance with the invention.

Referring now to FIG. 12, a schematic view of a stimulator 120 in accordance with the invention is illustrated. Digestive organ stimulators may include any stimulator that comprises an electrode electrically coupled to a digestive organ and configured to deliver a stimulating signal to the digestive organ. One example of such a stimulator is a device configured to stimulate a stomach comprising at least one electrode coupled to the stomach and a pulse generator coupled to the electrode. Such electrodes may be implanted at the stomach, e.g., either through open surgery, laparoscopically or endoscopically.

As illustrated in FIG. 12, a stimulator 120 in accordance with one example of the invention comprises a CPU 121 including a memory device 122 having lookup table 123 where stimulation parameters are associated with a random number, for example in a range of random numbers. A random number generator 124 is coupled to the CPU 121 and when prompted, randomly generates a number within a range corresponding to particular stimulation parameters. The random number generator, for example may have 100 possible random number corresponding to different parameters of a given type (e.g. 1-100 for pulse repetition rates and 101-200 for pulse widths, etc.) The random number generator may also have certain random numbers each corresponding to a particular predetermined signal to be delivered that may vary one or more parameters or may have varied shapes or types of stimulation signals.

The generated random number identifies a stimulation parameter or parameters stored in the lookup table 123 of the memory device 122. The CPU 121 then controls stimulation at the stimulation output 125 (e.g., to one or more electrodes) to deliver stimulation to a digestive organ where the stimulation corresponds to the randomly (or pseudorandomly) generated or selected stimulation parameter. More than one lookup table and random number generators may be used where multiple stimulation parameters are randomized.

Figure 10:
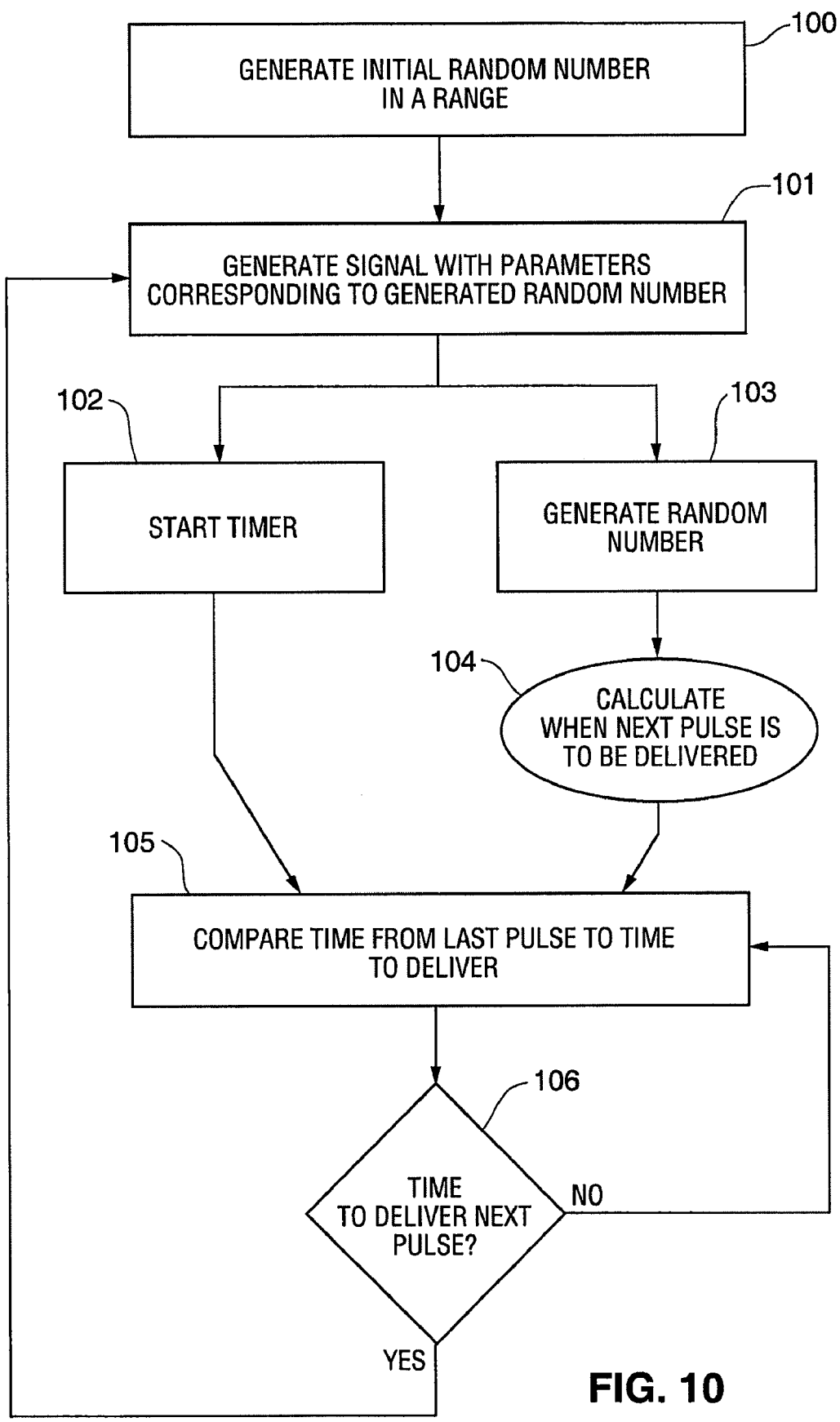
FIG. 10 is a flow chart illustrating operation of a stimulation device in accordance with the invention.

FIG. 10 illustrates an exemplary method and operation of a device in accordance with the invention. A random number is first generated (100) within a range of random numbers. Each random number corresponds to a particular stimulation signal or a stimulation parameter (or group of parameters) within a window or range of parameters. A pulse or burst of pulses with parameters corresponding to the generated random number is generated and delivered to a digestive organ for stimulation (101). Then a timer is started to identify when the first signal has been initiated (102) and a random number is again generated (103) corresponding to a particular stimulation signal of a stimulation parameter (or group of parameters). And, a calculation is made as to when the next stimulation pulse or burst of pulses is to be delivered (104). The calculation of the time for delivery may depend on which stimulation parameter is being randomized. If the pulse repetition rate or burst repetition rate is the varying parameter, the calculation of when the next pulse or burst of pulses respectively is to be delivered will be based on the variation in pulse or burst repetition rate. If the pulse repetition rate or burst repetition rate is constant, the calculation of the delivery time will be constant or based on the constant pulse or burst repetition rate. If the randomization is to occur periodically, the stimulation is delivered according to a protocol with a first set of stimulation patterns until a certain period determined, e.g. by the timer, has transpired. When the period has transpired, the next randomized stimulation parameters are then used according to a stimulation protocol. If the stimulation protocol involves turning stimulation on or off under various conditions, the timer may be turned on when the stimulation is on and turned off when the stimulation is off. Alternatively, the timer may run continuously.

The time for delivery of the next signal and the time of the timer (when the previous pulse or burst of pulses began) are compared to determine if it is time for the next pulse or burst of pulses to be delivered. If it is not time to deliver the next pulse or burst of pulses (106) then the comparison is made again (105) until it is time to deliver the next pulse or burst of pulses (106) whereupon a signal with parameters corresponding to the generated random number is generated (101) and steps 102-106 are repeated.

Figure 11:
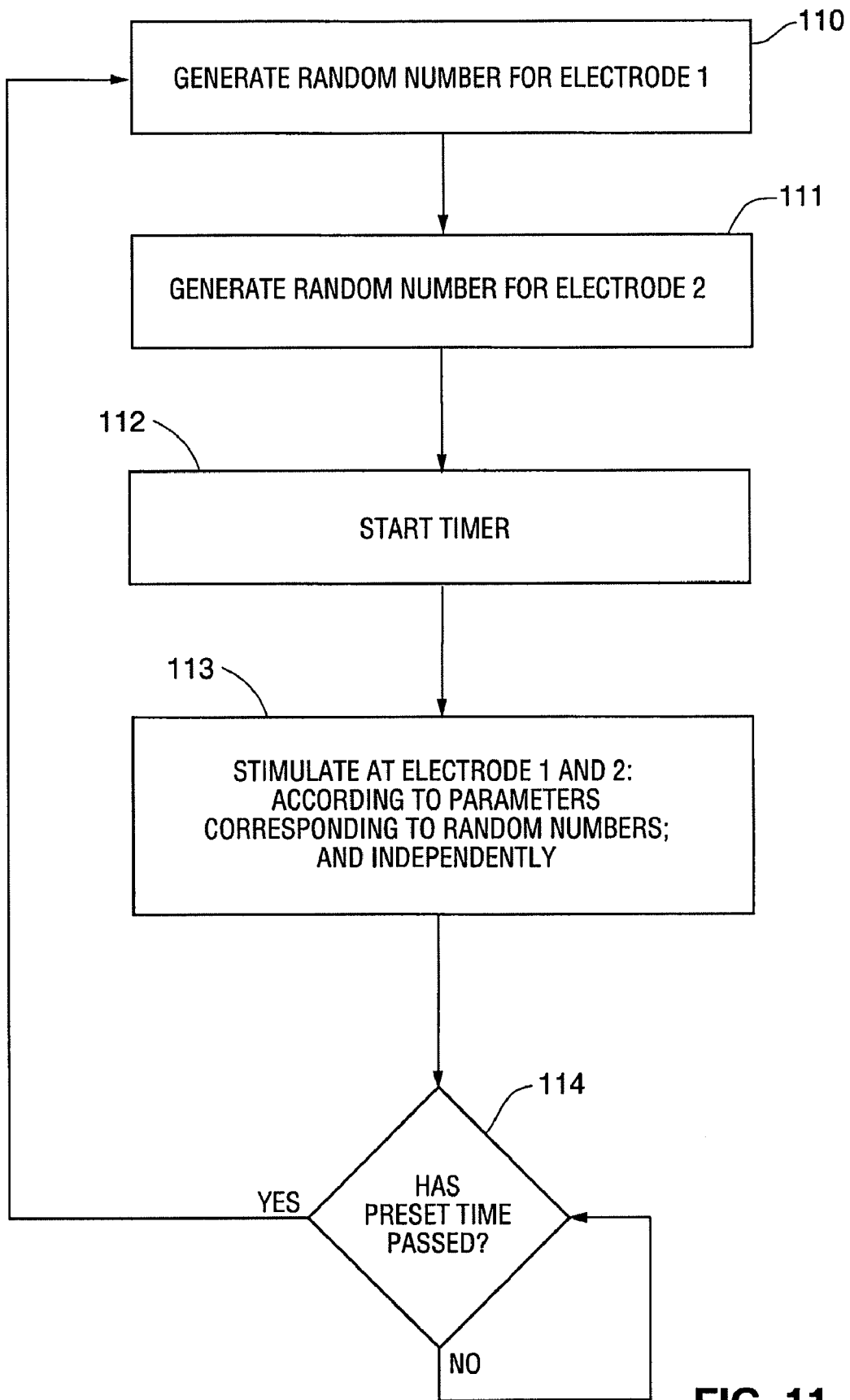
FIG. 11 is a flow chart illustrating operation of a stimulation device in accordance with the invention.

FIG. 11 illustrates a method and operation of a device in accordance with the invention. A random number for Electrode 1 is first generated (110) within a range of random numbers. A random number for Electrode 2 (111) is then generated within a range of random numbers. Each random number corresponds to a particular stimulation signal or a stimulation parameter (or group of parameters) within a window or range of parameters. A timer is then started (112) as a pulse or burst period begins. Pulses or bursts with parameters corresponding to each generated random number for Electrodes 1 and 2 are generated and delivered to a digestive organ for stimulation correspondingly at Electrodes 1 and 2 (113). These stimulation signals are independent of each other. They may, however be timed to fall within a predetermined pulse repetition rate so that generally the stimulation signals are each delivered within a preset period of time before the next set of stimulation signals are delivered to Electrodes 1 and 2. Thus, as set forth in step 112 a timer is started to identify the beginning of a first pulse period. It is then determined if the preset time has passed (114) at which time steps 111 to 114 are repeated.

While the invention has been described with reference to certain embodiments, it will be understood that variations and modifications may be made within the scope of the following claims. Such modifications may include substituting elements or components, which perform substantially the same function in substantially the same way to achieve substantially the same result that the invention can be practiced with modification within the scope of the following claims.

What is claimed is:

1. A digestive organ stimulator comprising:
   a stimulation signal generator;
   a selector coupled to the stimulation signal generator and configured to randomly select an initial signal parameter for stimulation of the digestive organ at non-physiologic rates, wherein the initial signal parameter is generated from a random number corresponding to a pre-selected stimulation parameter, wherein the random stimulation parameter is determined based on the random number;
   a stimulation output configured to be coupled to the digestive organ, wherein the stimulation signal generator is configured to output through the stimulation output, a stimulation signal comprising at least one randomly selected signal parameter; and
   a sensor for determining if a response to the stimulation signal is a desired response, wherein the sensor is coupled to the selector and the selector is configured to randomly select a subsequent parameter if the sensor senses a response that is not the desired response.

2. The digestive organ stimulator of claim 1 wherein the selector comprises a pseudorandom selector configured to pseudorandomly select-said at least one signal parameter.

3. The digestive organ stimulator of claim 1 wherein the at least one randomly selected signal parameter is selected from a group comprising: pulse width, pulse amplitude, pulse repetition rate, burst frequency, burst envelope, pulses per burst, pulse shape and burst repetition rate.

4. The digestive organ stimulator of claim 1 wherein the at least one randomly selected signal parameter is selected from a predetermined group of signal parameters.

5. The digestive organ stimulator of claim 1 further comprising:
   a plurality of outputs wherein the selector is configured to randomly select a signal parameter for each of said plurality of outputs to be delivered thereto.

6. The device of claim 1 wherein the selector is configured to select a parameter for each of a plurality of parameter types.

7. The device of claim 1 wherein the stimulation output comprises an electrode.

8. The device of claim 1 wherein the stimulation output comprises an electrode configured to be coupled to a gastrointestinal tract.

9. The device of claim 1 wherein the stimulation output comprises an electrode configured to be coupled to a stomach.

10. The device of claim 1 wherein the stimulation signal creates a sensation of satiety.

* * * * *